United States Patent
Ostanin et al.

(10) Patent No.: US 7,570,125 B2
(45) Date of Patent: Aug. 4, 2009

(54) CRYSTAL OSCILLATOR

(75) Inventors: Victor Petrovich Ostanin, Cambridge (GB); Alexander Sleptsov, Cambridge (GB)

(73) Assignee: Akubio Limited, Cambridge (GB)

( * ) Notice: Subject to any disclaimer, the term of this patent is extended or adjusted under 35 U.S.C. 154(b) by 99 days.

(21) Appl. No.: 10/553,321

(22) PCT Filed: Apr. 14, 2004

(86) PCT No.: PCT/GB2004/001615

§ 371 (c)(1),
(2), (4) Date: Jun. 14, 2006

(87) PCT Pub. No.: WO2004/095012

PCT Pub. Date: Nov. 4, 2004

(65) Prior Publication Data

US 2007/0040624 A1    Feb. 22, 2007

(30) Foreign Application Priority Data

Apr. 17, 2003 (GB) .................... 0308950.5
Sep. 12, 2003 (GB) .................... 0321443.4

(51) Int. Cl.
H03B 5/32 (2006.01)
(52) U.S. Cl. .................. 331/158; 331/175; 331/74; 331/116 R; 331/116 FE; 331/176; 324/76.52; 73/54.25
(58) Field of Classification Search .............. 331/158, 331/175, 176, 116 R, 116 FE, 74; 324/76.52; 73/54.25

See application file for complete search history.

(56) References Cited

U.S. PATENT DOCUMENTS

| | | | |
|---|---|---|---|
| 4,818,954 A | 4/1989 | Flachenecker et al. | |
| 5,416,448 A | 5/1995 | Wessendorf | |
| 6,041,642 A | 3/2000 | Duncan | |
| 6,820,469 B1 * | 11/2004 | Adkins et al. | 73/54.25 |
| 6,865,949 B2 | 3/2005 | Blakley | |
| 6,972,553 B2 * | 12/2005 | Petrovich et al. | 324/76.52 |
| 6,978,656 B2 | 12/2005 | Blakley | |
| 6,990,852 B2 | 1/2006 | Berndt | |
| 7,093,482 B2 | 8/2006 | Berndt | |
| 2005/0132812 A1 | 6/2005 | Blakley | |

FOREIGN PATENT DOCUMENTS

EP    1 528 394    5/2005
WO    WO 01/02857 A1    1/2001

* cited by examiner

OTHER PUBLICATIONS

F. N. Dultsev et al., "Direct and Quantitative Detection of Bacteriophage by 'Hearing' Surface Detachment using a Quartz Crystal Microbalance", Analytical Chemistry, American Chemical Society, vol. 73, No. 16, Aug. 15, 2001, pp. 3935-3939, XP-001089327.

*Primary Examiner*—Arnold Kinkead
(74) *Attorney, Agent, or Firm*—Blank Rome LLP

(57) ABSTRACT

An ocscillator circuit having: a) a piezoelectric crystal connected to a surface; b) a variable frequency generator for generating a driving signal which is supplied to the crystal to cause the crystal to oscillate, thereby causing the surface to oscillate; and, c) an analyser for monitoring the phase shift between the voltage across the crystal and the current flowing through it and, in response generating an adjustment signal which relates to the difference between the oscillation frequency and a resonant frequency of the crystal, the variable frequency generator being responsive to the adjustment signal to vary the frequency of the driving signal to cause the crystal to oscillate at the resonant frequency.

20 Claims, 3 Drawing Sheets

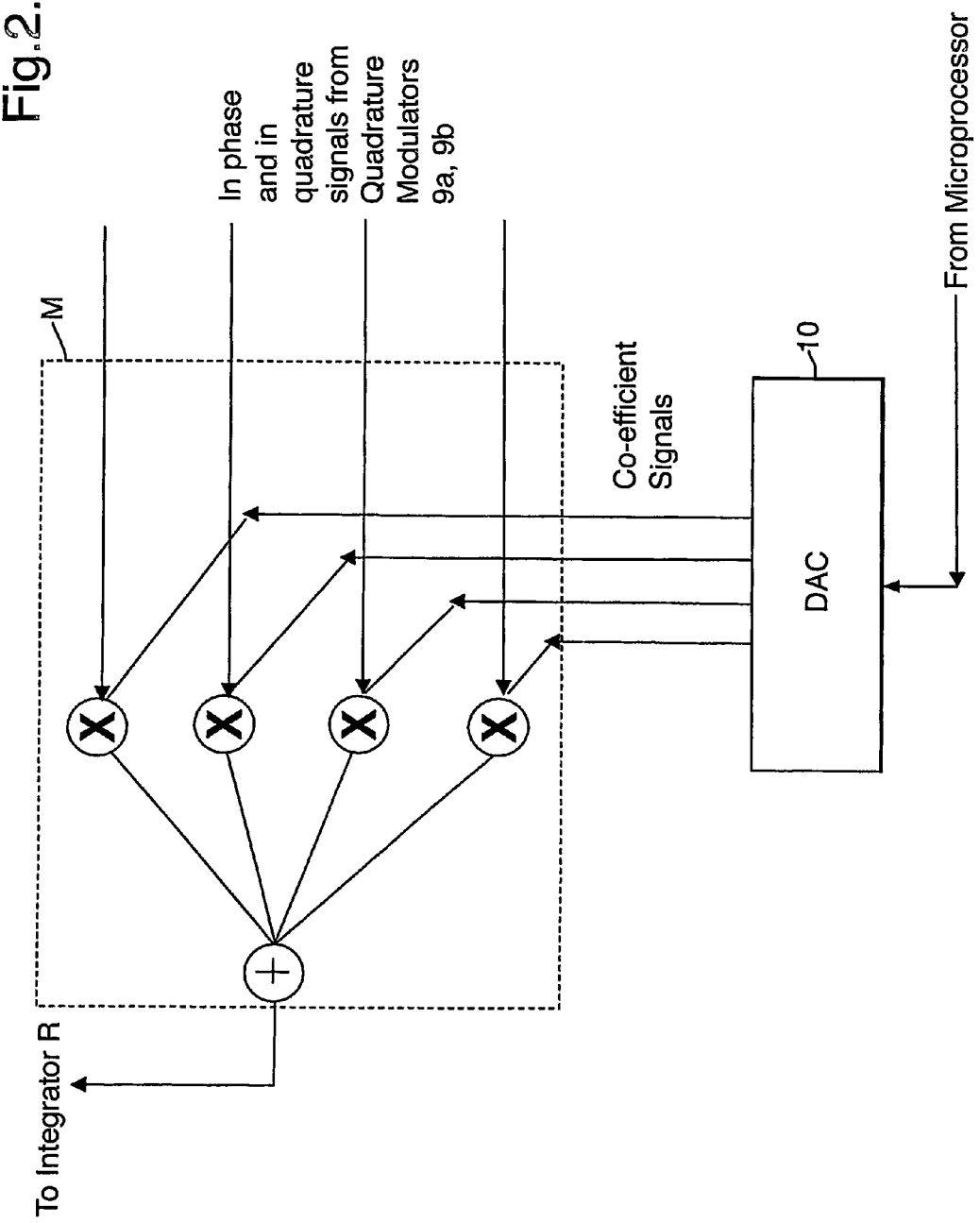

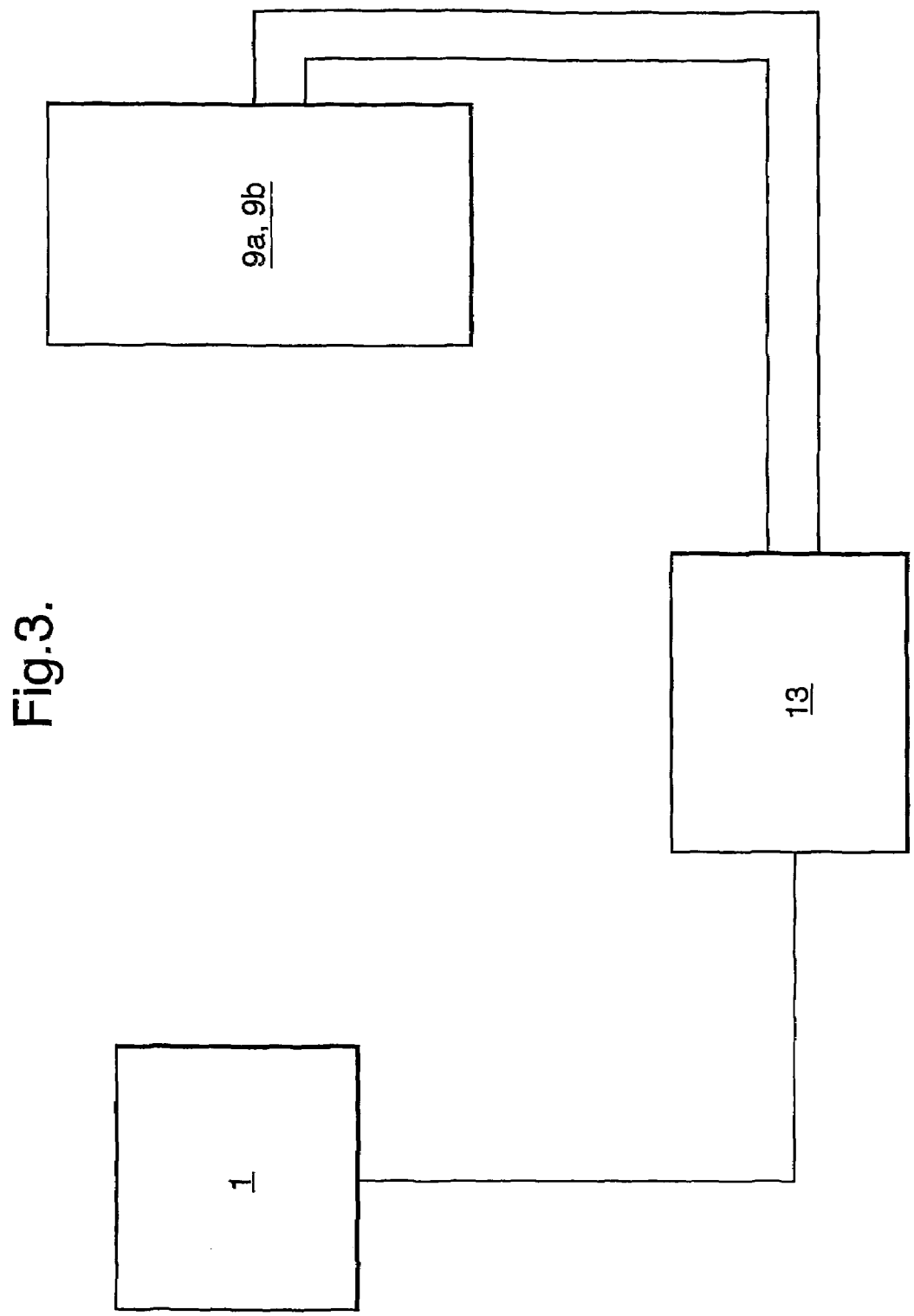

CRYSTAL OSCILLATOR

FIELD OF INVENTION

This invention relates to a crystal oscillator circuit for example, for use in sensors and a method of operation in which the crystal is caused to oscillate at a chosen resonant frequency, irrespective of changes in that frequency. The invention finds particular utility under conditions where high drive power and external influences cause unpredictable changes in the resonant frequency.

DESCRIPTION OF RELATED ART

In conventional applications of quartz crystal oscillators, such as timing and frequency control, the quartz crystal is connected in a resonant circuit and maintains a highly stable frequency of operation since, amongst other reasons, a low driving voltage is used. In these applications, the control of the driving voltage is not as important as the frequency of oscillation and maintaining the driving voltage at a low level avoids heating the crystal.

Quartz and other piezo-electric oscillators are widely used in sensing applications; for example, in the sensing of temperature, pressure, mass and viscosity. In such applications there is a need to ensure that the frequency stays on resonance, and methods for achieving this are known. They include temperature stabilisation, free-running oscillator circuits, and phase shifting networks. In all these cases the oscillator is operating at a fixed low power level and in its linear range However, there are applications, for example sensor applications, of quartz crystals where the driving power is required to be varied over a much wider range, including power levels which drive the crystal into its non-linear mode of operation. For example, the quartz crystal may be used as a motional transducer. Such an application is rupture event scanning (REVS™) which is described in WO01/02857. In this application, the driving voltages are typically up to 20 volts peak to peak. It is well known that as the driving voltage increases, the resonant frequency of the crystal changes. This is due to a number of effects, such as irreversible voltage induced changes in the quartz structure caused by the nonlinear response of the quartz crystal to high voltages and temperature dependence of the crystal's resonant frequencies caused by the heating of the crystal at high power levels.

In conventional oscillator applications, the oscillator selects the strongest mode. Spurious modes exist in crystals whose power versus frequency characteristics may approach or cross that of the resonance at higher power. These interactions can change the resonant response of the crystal. Spurious modes close to the resonance which are normally of low intensity may have a steep frequency versus temperature characteristic. At a certain temperature, the frequency of an unwanted mode may coincide with the oscillator frequency. Both these effects can cause a "mode hop" or abrupt change in the frequency of the oscillator.

Furthermore, in many sensors it is desirable to operate at a resonant overtone of the crystal, because sensitivity of some parameters is increased at higher frequencies. However as the overtone frequency increases, the density of spurious modes also increases, and the probability of mode-hopping increases. Unwanted modes can be controlled by proper design and fabrication methods for low power applications; however, as the power level increases this becomes increasingly difficult.

In the REVS™ process, the power level may typically be varied from zero to 250 mW, and this must be done in a controlled way while maintaining the oscillation at resonance. Any deviation from the resonance will cause the amplitude of the mechanical motion of the crystal to decrease. Since identification of a rupture event is dependent on the control of mechanical motion such deviations cannot be tolerated.

The problems described below are exacerbated in rupture event scanning where the crystal is in contact with a dissipative fluid. As the amplitude increases non-linear visco-elastic effects change the frictional forces on the crystal in an unpredictable way. Dissipative losses in the fluid may also cause heating of the crystal. These effects can cause changes in the resonant frequency of the crystal as the power is increased.

SUMMARY OF THE INVENTION

Thus, in REVS™ there is a need to have a frequency control system which actively drives the crystal always on resonance, and which can follow unpredictable changes in the resonant frequency due to thermal and non-linear effects, while maintaining control over the drive power supplied.

In accordance with one aspect of the present invention, there is provided an apparatus for oscillating a surface, the apparatus comprising an oscillator circuit having:
  a) a piezoelectric crystal connected to the surface;
  b) a variable frequency generator for generating a driving signal which is supplied to the crystal to cause the crystal to oscillate, thereby causing the surface to oscillate; and,
  c) an analyser for monitoring the phase shift between the voltage across the crystal and the current flowing through it and, in response, generating an adjustment signal which relates to the difference between the oscillation frequency and a resonant frequency of the crystal, the variable frequency generator being responsive to the adjustment signal to vary the frequency of the driving signal to cause the crystal to oscillate at the resonant frequency.

In accordance with a second aspect of the present invention there is provided a method for oscillating a surface, the method comprising:
  a) producing a driving signal that causes a piezoelectric crystal connected to the surface to oscillate thereby causing the surface to oscillate;
  b) monitoring the phase shift between the voltage across the crystal and the current flowing through it and, in response, generating an adjustment signal which relates to the difference between the oscillation frequency and a resonant frequency of the crystal; and,
  c) varying the frequency of the driving signal in accordance with the adjustment signal such that the crystal oscillates at the resonant frequency.

Hence, the invention provides an apparatus and method for oscillating a surface by oscillating a piezoelectric crystal connected to the surface such that the crystal oscillates at one of its resonant frequencies, irrespective of changes in that frequency.

Typically, the variable frequency generator comprises a frequency synthesiser which is supplied by a reference frequency. This reference frequency may be temperature stabilised in the form of an oven control crystal oscillator or alternatively may be a voltage controlled reference in the form of a voltage controlled crystal oscillator.

In a preferred embodiment, the variable frequency generator additionally generates a quadrature signal that is shifted in phase by 90° from the driving signal. In this event, the analyser typically comprises two quadrature modulators, one receiving the driving signal, the quadrature signal and a signal representing the voltage across the crystal and the other receiving the driving signal, the quadrature signal and a signal representing the current flowing through the crystal. Typically, the adjustment signal is related to the phase shift between the voltage and the current.

The adjustment signal may control the operation of the frequency synthesiser directly therefore changing the frequency of the driving signal or alternatively the adjustment signal may control the frequency of oscillation of the voltage controlled crystal oscillator, if present.

Preferably, a voltage controlled amplifier is used to control the amplitude of oscillation of the crystal.

BRIEF DESCRIPTION OF THE DRAWING

An embodiment of the invention will now be described with reference to the accompanying drawings in which:

FIG. 2 shows a detailed view of part of FIG. 1; and,

FIG. 3 shows an alternative implementation for part of FIG. 1.

DETAILED DESCRIPTION OF THE PREFERRED EMBODIMENT

Figure 1:
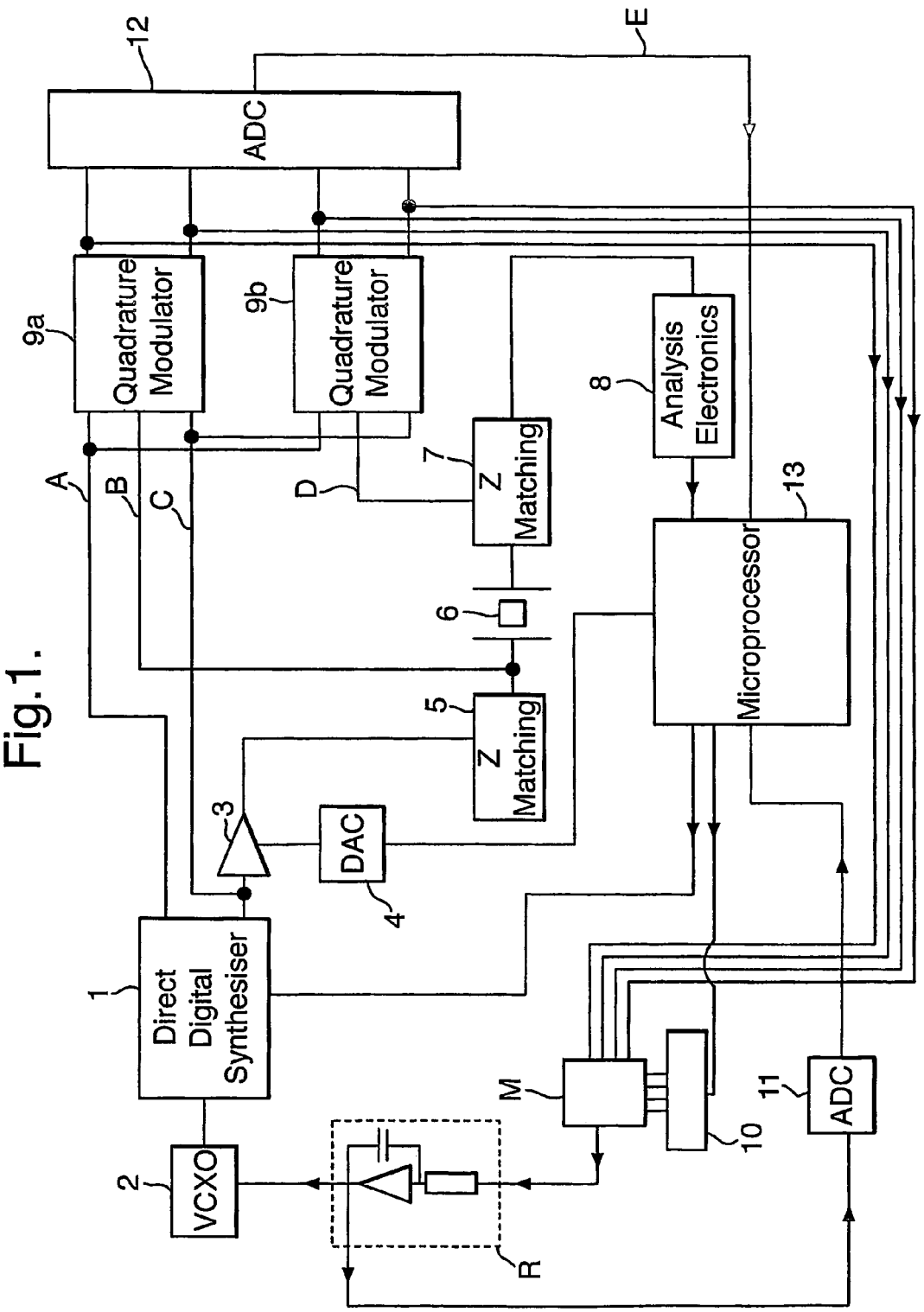
FIG. 1 shows, schematically, apparatus for performing the invention.

FIG. 1 shows a high resolution frequency synthesiser 1 which produces a driving signal, on line C, that is supplied to a voltage controlled amplifier 3 and to quadrature modulators 9a, 9b. The frequency synthesiser 1 also produces a quadrature signal, on line A, that is supplied to the quadrature modulators 9a, 9b. A voltage controlled crystal oscillator (VCXO) 2 is used as a reference frequency for the frequency synthesiser 1. The signal produced by the VCXO 2 is proportionally converted by the frequency synthesiser 1 into the frequency at which the driving signal and quadrature signal output by the frequency synthesiser 1 oscillate.

Such frequency synthesisers are well known in the art. The AD9854 made by Analog Devices is a suitable example. This digitally synthesises a precision sinusoidal signal at a programmable frequency using a high frequency reference oscillator. In the example, the synthesis of a typical 14.2 MHz signal suitable for use in REVS™ can be achieved using a 20 MHz VCXO reference. The typical stability of the frequency synthesiser output is <0.1 Hz.

The amplitude of the driving signal is controlled by a voltage controlled amplifier (VCA) 3, the gain of which is under control of microprocessor 13 which causes digital to analogue converter (DAC) 4 to supply an appropriate control signal to VCA 3. The output from VCA 3 drives a piezoelectric crystal 6 via an impedance matching network 5. The impedance matching network 5 ensures that the output from the VCA 3 is matched in impedance with the crystal 6 such that energy is efficiently coupled into the crystal 6.

The crystal 6 is also connected to quadrature modulator 9a in order to supply this with a signal representing the voltage across the crystal 6.

The crystal 6 is connected to a second impedance matching network 7 which couples the signal energy from the crystal 6 into a set of analysis electronics 8 that are connected to the microprocessor 13. The analysis electronics 8 perform the signal extraction required for rupture event scanning.

The network 5 is configured such that it presents a high impedance to frequencies other than those at or near the drive frequency. Conversely, the network 7 is configured such that it presents a high impedance to frequencies other than those at or near the detection frequency. Thus, network 7 provides a virtual ground to the drive frequency, and the signal in line B can be used as an input to quadrature modulator 9a.

The second impedance matching network 7 also provides a signal representing the current flowing through the crystal 6 to quadrature modulator 9b.

The signals representing the voltage across the crystal 6 and the current flowing through it, present on lines B and D respectively, are both shifted in phase with respect to the driving signal from frequency synthesiser 1, due to the reactive impedance characteristics of the circuit and the configuration of the hardware.

At resonance, the impedance of the crystal 6 is at a minimum and is entirely resistive in nature. The resistive impedance is determined by the motional resistance of the crystal 6 and the viscous energy dissipation in the fluid in contact with the crystal. A typical value for this in a rupture event scanning application is 200 ohms. Since the impedance of the crystal is resistive at resonance, it is possible to determine that the crystal is oscillating at a resonant frequency by measuring the phase shift between the voltage developed across the crystal 6 and the current flowing through it. At resonance, this phase shift will be zero. In effect, the phase shift provides an indication of the difference between the resonant frequency and the actual frequency of oscillation.

It is an essential requirement for an application such as REVS™ that the power delivered to the crystal is controlled smoothly and preferably linearly in response to the gain of amplifier 3. Phase shifts between current and voltage at the crystal cause uncontrolled deviations in the amplitude of oscillation and thus, must be minimised as much as possible. This is carried out by a phase modulator array M and DAC (10).

As previously described, a signal representing the voltage across the crystal 6 is supplied to quadrature modulator 9a and a signal representing current flowing through the crystal 6 is supplied to quadrature modulator 9b. These quadrature modulators 9a, 9b mix the respective voltage and current signals with the driving and quadrature signals produced by the frequency synthesiser 1 to produce four output signals, two from quadrature modulator 9a and two from quadrature modulator 9b.

Quadrature modulators are well known components and the output signals from quadrature modulator 9a represent the real and imaginary components of the voltage across the crystal 6 and the outputs from quadrature modulator 9b represent the real and imaginary components of the current flowing through the crystal 6. These four signals are supplied to an analogue to digital converter (ADC) 12 which supplies digital representations of these to microprocessor 13, via four line bus E. This information can be used to provide a true driver power co-ordinate in the rupture event scanning analysis.

The compensation signal used for frequency adjustment is provided by the modulator array M and DAC 10. Modulator array M is an array of potentiometers controlled by DAC 10. DAC 10 applies weighting signals to the voltage and current components outputs from quadrature modulators 9a, 9b according to coefficients. that are set via an input from microprocessor 13. This is shown in more detail in FIG. 2. Alternatively, modulator array M and DAC 10 can be combined in an array of digitally controlled potentiometers.

The weighting coefficients applied by the DAC 10 are such that if a purely resistive load is placed in the position of the crystal 6, then when the weighted signals are added, the resulting signal is restored to being in phase with the reference signal of frequency synthesiser 1.

The coefficients can be determined by calibrating the circuit with a purely resistive load and once established can be used for a specified drive frequency, or circuit configuration.

As described earlier, when driving at high powers with a dissipative load the resonance frequency of the oscillator may be susceptible to drift and unpredictable changes. Any such changes will bring about an additional phase shift at the output of the modulator array.

This phase shifted signal is integrated over time by the integrating regulator R, the output of which drives VCXO 2. Thus, as the resonant frequency of the crystal drifts, this will cause the phase to shift, producing a compensating change in the output of the modulator array M, which then corrects the drive frequency of the frequency synthesiser 1. The phase shift output of the regulator R can also be connected to the microprocessor 13, for further analysis.

Therefore, the frequency of the driving and quadrature signals produced by frequency synthesiser 1 can be caused to follow the changes in the resonant frequency of the crystal 6 by altering the frequency of oscillation of VCXO 2 directly via the output of the DAC 10.

Although the method described above is analogue, it is also possible to use digital or hybrid methods to achieve the same effect.

In a digital implementation, the phase shift between the four outputs of quadrature modulators 9a, 9b, representing the voltage across crystal 6 and the current flowing through it, is calculated by software running on microprocessor 13. This operates on the digital representations of the real and imaginary components of the voltage across crystal 6 and the current flowing through it received from ADC 12, via bus E, and thereby adjusting the operation of frequency synthesiser 1.

A digital implementation is shown in FIG. 1 where the four digitised signals (bus E) from ADC 12 (being digital representations of the outputs from quadrature modulators 9a, 9b) are read and processed by microprocessor 13, and the phase difference between the voltage across crystal 6 and the current flowing through it is calculated. The microprocessor 13 then integrates the phase difference and calculates the digital input signal necessary to adjust the frequency of oscillation of the frequency synthesiser 1 to follow the resonant frequency of the crystal 6. If the VCXO 2 is absent in this arrangement, the frequency synthesiser 1 must have a high resolution, typically <0.1 Hz, and the ability to smoothly change frequency. Suitable devices are commercially available.

FIG. 3 shows an alternative arrangement in which quadrature modulators 9a, 9b supply digital signals directly to microprocessor 13.

The two operations of phase calculation, and frequency control can each be either digital or analogue. There may be advantages in operation,of such a hybrid system. For example, it is quite demanding to carry out the phase calculation and integration digitally in real time, so an analogue operation may produce more effective control, combined with a digital drive to frequency synthesiser 1.

As such, by monitoring the voltage across the crystal 6 and current flowing through it, it is possible for the frequency of the driving signal supplied to it by frequency synthesiser 1 to be adjusted such that the crystal 6 is always forced to oscillate at the resonant frequency, irrespective of variations in that frequency.

With respect to a rupture event scanning application, the crystal 6 is desired to oscillate at one of its series resonant frequencies. Since the characteristics of each crystal are unique in their own right and depend on the characteristics of the fluid with which it is in contact, the crystal is first pres-canned whilst in contact with the fluid before performing the analysis in order to determine its resonant frequency.

The frequency of the driving signal is first increased in, for example, 5 kHz steps from a value close to the nominal resonant frequency whilst maintaining the amplitude of the driving signal at a low amplitude. The voltage across the crystal 6 and the current flowing through it are measured at each step. The phase shift between these is then used to determine an estimate of the resonant frequency. When close to resonance the variation of phase shift with frequency is linear. Therefore, the phase versus frequency data can be extrapolated to zero phase and the resonant frequency approximately determined.

The frequency of the driving signal is then increased in smaller steps, for example 50 Hz, in a smaller range around the resonant frequency. The phase difference is again measured, and then the resonant frequency can be determined precisely by interpolation. Alternatively, the coarse data can be fitted to the known variation of phase with frequency, and the resonant frequency determined directly.

The invention claimed is:

1. An apparatus for oscillating a surface, the apparatus comprising an oscillator circuit having:
   a) a piezoelectric crystal connected to the surface;
   b) a variable frequency generator for generating a driving signal which is supplied to the crystal to cause the crystal to oscillate, thereby causing the surface to oscillate; and
   c) an analyzer for monitoring the phase shift between the voltage across the crystal and the current flowing through it and, in response, generating an adjustment signal which relates to the difference between the oscillation frequency and a resonant frequency of the crystal, the variable frequency generator being responsive to the adjustment signal to vary the frequency of the driving signal to cause the crystal to oscillate at the resonant frequency;
   wherein the variable frequency generator comprises a frequency synthesizer and additionally generates a quadrature signal that is shifted in phase by 90° from the driving signal.

2. Apparatus according to claim 1, wherein the analyzer comprises two quadrature modulators, one receiving the driving signal, the quadrature signal and a signal representing the voltage across the crystal and the other receiving the driving signal, the quadrature signal and a signal representing the current flowing through the crystal.

3. Apparatus according to claim 2, wherein the adjustment signal controls the operation of the frequency synthesizer, thereby changing the frequency of the driving signal.

4. Apparatus according to claim 1, wherein said apparatus is configured to separate from the surface an analyte that has been immobilized on the surface.

5. An apparatus for oscillating a surface, the apparatus comprising an oscillator circuit having:
   a) a piezoelectric crystal connected to the surface;
   b) a variable frequency generator for generating a driving signal which is supplied to the crystal to cause the crystal to oscillate, thereby causing the surface to oscillate; and,
   c) an analyzer for monitoring the phase shift between the voltage across the crystal and the current flowing through it and, in response, generating an adjustment signal which relates to the difference between the oscillation frequency and a resonant frequency of the crystal, the variable frequency generator being responsive to the adjustment signal to vary the frequency of the driving signal to cause the crystal to oscillate at the resonant frequency;

wherein the variable frequency generator comprises a frequency synthesizer, and wherein the frequency synthesizer is supplied by a reference frequency from an oven controlled crystal oscillator.

6. Apparatus according to claim 5, wherein said apparatus is configured to separate from the surface an analyte that has been immobilized on the surface.

7. An apparatus for oscillating a surface, the apparatus comprising an oscillator circuit having:
   a) a piezoelectric crystal connected to the surface;
   b) a variable frequency generator for generating a driving signal which is supplied to the crystal to cause the crystal to oscillate, thereby causing the surface to oscillate; and
   c) an analyzer for monitoring the phase shift between the voltage across the crystal and the current flowing through it and, in response, generating an adjustment signal which relates to the difference between the oscillation frequency and a resonant frequency of the crystal, the variable frequency generator being responsive to the adjustment signal to vary the frequency of the driving signal to cause the crystal to oscillate at the resonant frequency;
   wherein the variable frequency generator comprises a frequency synthesizer, and wherein the frequency synthesizer is supplied by a reference frequency from a voltage controlled crystal oscillator.

8. Apparatus according to claim 7, wherein the adjustment signal controls the frequency of oscillation of the voltage controlled crystal oscillator thereby changing the frequency of the driving signal.

9. Apparatus according to claim 7, wherein the variable frequency generator additionally generates a quadrature signal that is shifted in phase by 90° from the driving signal.

10. Apparatus according to claim 9, wherein the analyzer comprises two quadrature modulators, one receiving the driving signal, the quadrature signal and a signal representing the voltage across the crystal and the other receiving the driving signal, the quadrature signal and a signal representing the current flowing through the crystal.

11. Apparatus according to claim 7, wherein said apparatus is configured to separate from the surface an analyte that has been immobilized on the surface.

12. An apparatus for oscillating a surface, the apparatus comprising an oscillator circuit having:
   a) a piezoelectric crystal connected to the surface;
   b) a variable frequency generator for generating a driving signal which is supplied to the crystal to cause the crystal to oscillate, thereby causing the surface to oscillate;
   c) an analyzer for monitoring the phase shift between the voltage across the crystal and the current flowing through it and, in response, generating an adjustment signal which relates to the difference between the oscillation frequency and a resonant frequency of the crystal, the variable frequency generator being responsive to the adjustment signal to vary the frequency of the driving signal to cause the crystal to oscillate at the resonant frequency; and
   d) a voltage controlled amplifier for controlling the amplitude of oscillation of the crystal.

13. Apparatus according to claim 12, further comprising an impedance matching network, wherein the output from the voltage controlled amplifier drives the piezoelectric crystal via said network such that the output of the voltage controlled amplifier is matched in impedance with the piezoelectric crystal.

14. Apparatus according to claim 13, wherein the piezoelectric crystal is connected to a second impedance matching network.

15. Apparatus according to claim 12, wherein said apparatus is configured to separate from the surface an analyte that has been immobilized on the surface.

16. A method for oscillating a surface, the method comprising:
   a) producing a driving signal that causes a piezoelectric crystal connected to the surface to oscillate thereby causing the surface to oscillate;
   b) monitoring the phase shift between the voltage across the crystal and the current flowing through it and, in response, generating an adjustment signal which relates to the difference between the oscillation frequency and a resonant frequency of the crystal; and
   c) varying the frequency of the driving signal in accordance with the adjustment signal such that the crystal oscillates at the resonant frequency;
   wherein the driving signal is produced by frequency synthesis from a reference frequency, and wherein the reference frequency is temperature stabilized.

17. A method for oscillating a surface, the method comprising:
   a) producing a driving signal that causes a piezoelectric crystal connected to the surface to oscillate thereby causing the surface to oscillate;
   b) monitoring the phase shift between the voltage across the crystal and the current flowing through it and, in response, generating an adjustment signal which relates to the difference between the oscillation frequency and a resonant frequency of the crystal; and
   c) varying the frequency of the driving signal in accordance with the adjustment signal such that the crystal oscillates at the resonant frequency;
   wherein the driving signal is produced by frequency synthesis from a reference frequency, and wherein the reference frequency is voltage controlled.

18. A method for oscillating a surface, the method comprising:
   a) producing a driving signal that causes a piezoelectric crystal connected to the surface to oscillate thereby causing the surface to oscillate;
   b) monitoring the phase shift between the voltage across the crystal and the current flowing through it and, in response, generating an adjustment signal which relates to the difference between the oscillation frequency and a resonant frequency of the crystal;
   c) varying the frequency of the driving signal in accordance with the adjustment signal such that the crystal oscillates at the resonant frequency; and
   d) controlling the amplitude of oscillation of the crystal.

19. A method according to claim 18, wherein the voltage across and current flowing through the crystal are monitored and the adjustment signal is related to the phase shift between the voltage and current.

20. A method according to claim 19, wherein a quadrature signal that is in quadrature with the driving signal is also produced, the driving signal and quadrature signal both being mixed with a signal representing the voltage across the crystal and with a signal representing the current flowing through the crystal.

* * * * *